United States Patent [19]

Pinches et al.

[11] 4,449,048

[45] May 15, 1984

[54] WORKPIECE POSITIONING SYSTEM FOR BETA RAY MEASURING INSTRUMENTS

[75] Inventors: Philip B. Pinches, New York; Sidney Lieber, Kings Point, both of N.Y.

[73] Assignee: UPA Technology, Inc., Syosset, N.Y.

[21] Appl. No.: 426,717

[22] Filed: Sep. 29, 1982

[51] Int. Cl.³ ............................................. G01N 23/00
[52] U.S. Cl. .................................. 250/308; 250/491.1
[58] Field of Search ................. 250/308, 358.1, 359.1, 250/491.1; 356/16

[56] References Cited

U.S. PATENT DOCUMENTS

| | | | |
|---|---|---|---|
| 3,483,375 | 12/1969 | Joffe et al. | 250/491.1 |
| 3,588,507 | 6/1971 | Weinstock et al. | 250/308 |
| 3,720,833 | 3/1973 | Hay | 250/308 |

Primary Examiner—Janice A. Howell
Attorney, Agent, or Firm—Robert E. Isner

[57] ABSTRACT

A beta backscatter type of measuring instrument including a workpiece positioning system to permit precise prepositioning of the workpiece surface to be subjected to radiation preparatory to moving the radiation source into operative proximity therewith.

5 Claims, 7 Drawing Figures

WORKPIECE POSITIONING SYSTEM FOR BETA RAY MEASURING INSTRUMENTS

This invention relates to instruments for the nondestructive measurement of thin coatings on basal substrates by beta ray backscatter techniques and more particularly to an improved optical system for beta ray measuring instruments for precisely locating the area of a specimen to be subjected to radiation preparatory to moving the radiation source into proximity therewith.

Beta ray backscatter measuring instruments have been extensively utilized to measure the thicknesses of metallic deposits and coatings of various materials such as, for example, the conductive platings on printed circuit boards or the like. These instruments generally include a source of beta radiation, conveniently a radioactive isotope. This source emits radiation which is directed to strike a metallic coating and the radiation backscattered from the coating is measured by a detector in the form of a Geiger-Muller tube. An associated electronic counter or readout unit converts the output of the detector into utilizable intelligence. The accuracy and sensitivity of beta ray backscatter-type instruments is largely dependent upon the geometry of the system, that is, the geometric or positional relationship between the source, workpiece and detector, and to this end auxiliary means for locating the workpiece relative to the source and detector are usually incorporated, in accordance with the dictates of the workpiece configuration, as a component of most such measuring systems. In the operation of such units the beta radiation source must be placed in close proximity to the surface to be measured and the area to be radiated is generally defined by an aperture in a mask disposed intermediate the beta radiation source and the speciman and with the mask normally being disposed in interfacial abutting relation with the latter.

While such type instruments are highly useful in the nondestructive measurements of thin coatings on basal substrates, problems have arisen, compounded by the continued drive toward miniaturization, in properly locating and precisely controlling the area of a specimen to be exposed to radiation, as well as in maximizing the areas to be exposed to radiation when the radiation source is necessarily disposed remote therefrom to permit specimen positioning.

This invention may be briefly described, in its broader aspects, as a beta ray backscatter measuring instrument that incorporates an improved optical positioning system for precisely prelocating the specific area of a specimen to be subjected to radiation preparatory to moving a remote beta radiation source along a predetermined path into operative proximity therewith. In its narrower aspects, the subject invention includes the provision of an optical positioning system for beta ray backscatter and like measuring instruments that provides a clear visual indication of the exact area of exposure on the surface of a workpiece while the radiation source and the exposure area defining mask associated therewith are remotely located with respect thereto.

Among the advantages of the subject invention is the provision of a markedly improved workpiece positioning system for beta ray backscatter measuring instruments and the like that provides a clear and parallax free visual image of the exact area of exposure to beta radiation on the workpiece surface when the radiation source and exposure area defining mask are disposed remote therefrom and the concomitant permitted precise prepositioning of a workpiece preparatory to moving the radiation source into proximity therewith. Still further advantages include the provision of a visual image of an area that is identical with that of the area of exposure as defined by the aperture in the mask member associated with the beta ray source, which not only permits preselection of the size and shape of the exposure area in accord with the characteristics of the workpiece but also facilitates measurements adjacent to edge portions of coatings and permits the use of maximized areas of exposure for increased measurement accuracy. A still further advantage of this invention is the permitted preselection and use of varying shapes and sizes of exposure areas and accompanying visual observation thereof at the situs of measurement preparatory to initiation of exposure, all to the end of providing a significant extension of the effectiveness of beta backscatter type of measuring instruments.

The primary object of this invention is the provision of an improved system for precise prelocation of exposure areas on workpieces in beta backscatter thickness measuring instruments.

Another object of this invention is the provision of an improved optical system for providing a visual indicator on a workpiece surface of the exact area of beta ray exposure preparatory to moving a remotely located radiation source into operative proximity therewith.

Other objects and advantages of the subject invention will become apparent from the following portion of the specification and from the accompanying drawings which illustrate, in accord with the mandate of the patent statutes, a presently preferred embodiment incorporating the principles of the present invention.

Referring to the drawings.

Figure 1:
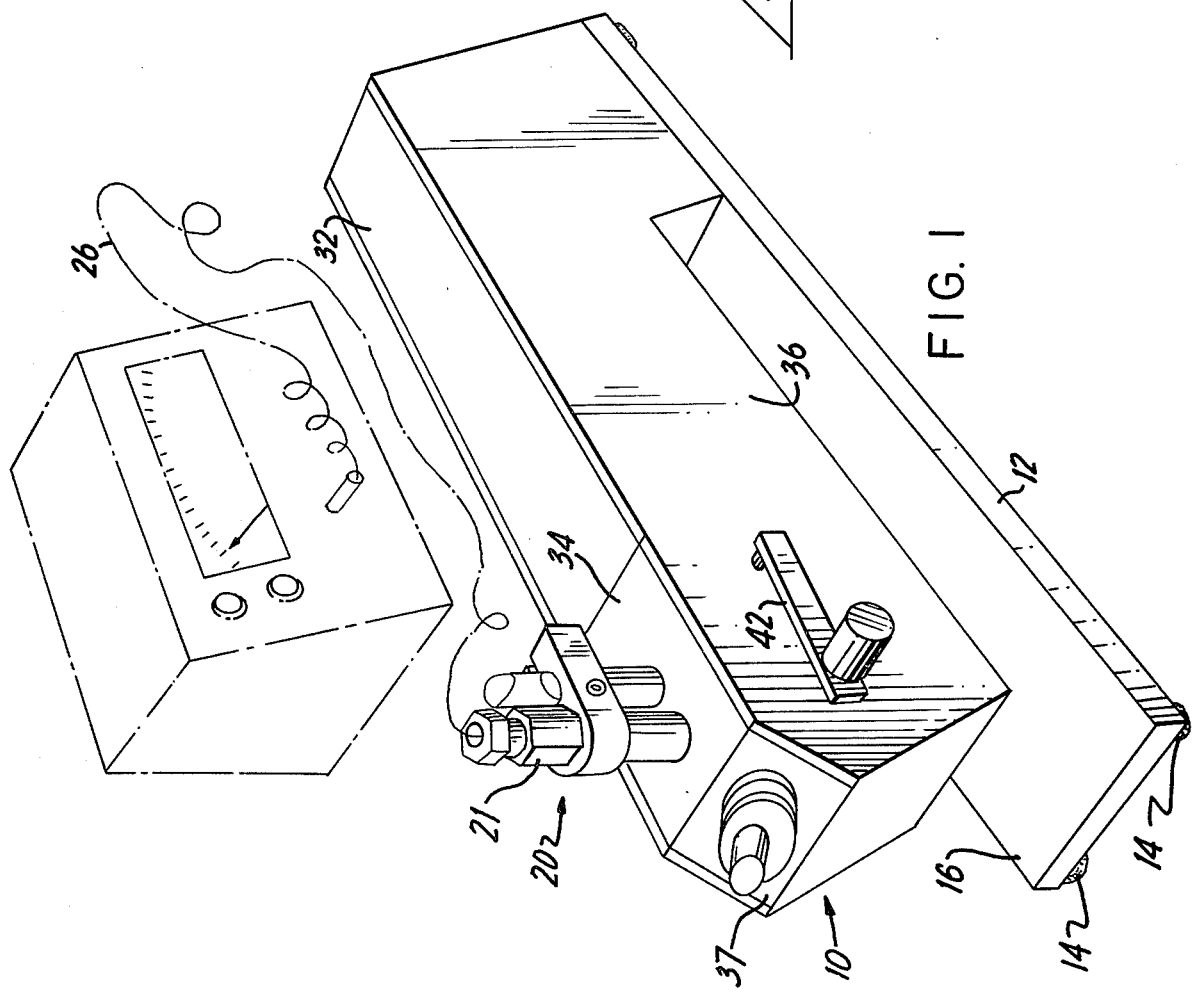
FIG. 1 is an oblique view of the apparatus incorporating the present invention.

Referring to the drawings and initially to FIG. 1 there is provided a probe system portion 10 of a beta backscatter type instrument for measuring the effective thickness in the plated coatings on basal substrates, such as, for example, printed circuit boards. Apart from the hereinafter described optical system, the beta backscatter probe system 10 may be of any suitable type and for illustrative purposes is suitably of the general type and character disclosed in U.S. Pat. No. 3,720,833. As shown, the apparatus 10 includes an elongate rectangular base member 12 supported on corner pedestals 14 which provides a horizontal workpiece supporting surface 16.

Incorporated therein is a conventional probe assembly 20 comprising an elongate hollow member or casing 21 having an exposure opening 22 defined by a mask 18 at one end. Mounted within the casing adjacent to the exposure opening 22 is a beta ray emitting radioactive isotope source contained in a relatively small holder or cup 23 and a beta radiation detector 24, suitably a Geiger-Muller tube, disposed above cup or holder 23 and having its window 25 arranged in fixed relation to the holder 23 and to the opening 22 of the casing. As is conventional, the output of the detector 24 is transmitted through a cable 26 to a readout or scaler unit as shown in FIG. 1 for conversion to utilizable intelligence.

As illustrated, the plane of the exposure opening 22 is perpendicular to the longitudinal axis of the probe assembly and the source holder or cup 23 is so located and supported as to direct a beam of radiation in the nature of an expanding cone axially with respect to the plane of the opening 22 and coincident with the longitudinal axis of the casing 21. Additionally, the source holder 23 is so constituted as to shield the window 25 of the detector from direct exposure to radiation from the contained radioisotope and together with its mounting is of diminutive size so as to minimize interference with the backscatter from the workpiece. The exposure opening 22 in the mask 18 may be of any desired shape such as rectangular, circular or any other desired geometric configuration to suit the particular needs of any given situation. In order to accommodate different shapes of exposure opening, the mask 18 is removably secured to the casing 21 as by a plurality of screws or the like.

The above described probe assembly 20 is illustratively mounted on and supported within an assembly of the general type shown in U.S. Pat. No. 3,720,833 in a manner to enable it to be moved in a predetermined path toward and away from a workpiece that has been precisely prelocated on the workpiece supporting surface 16 of the instrument.

Figure 3:
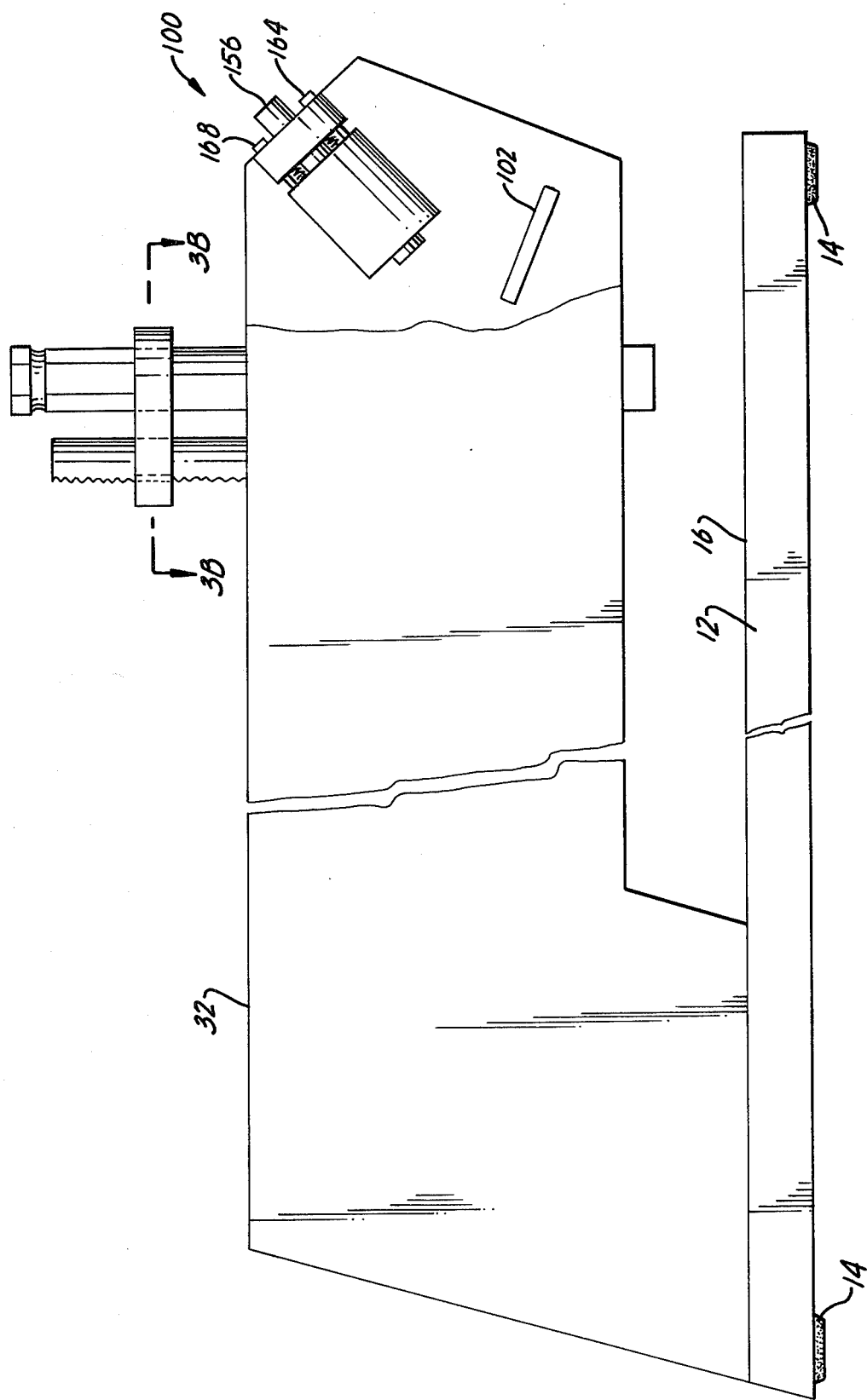
FIG. 3 is a side elevation partially in section of the apparatus illustrated in FIG. 1.
Figure 3A:
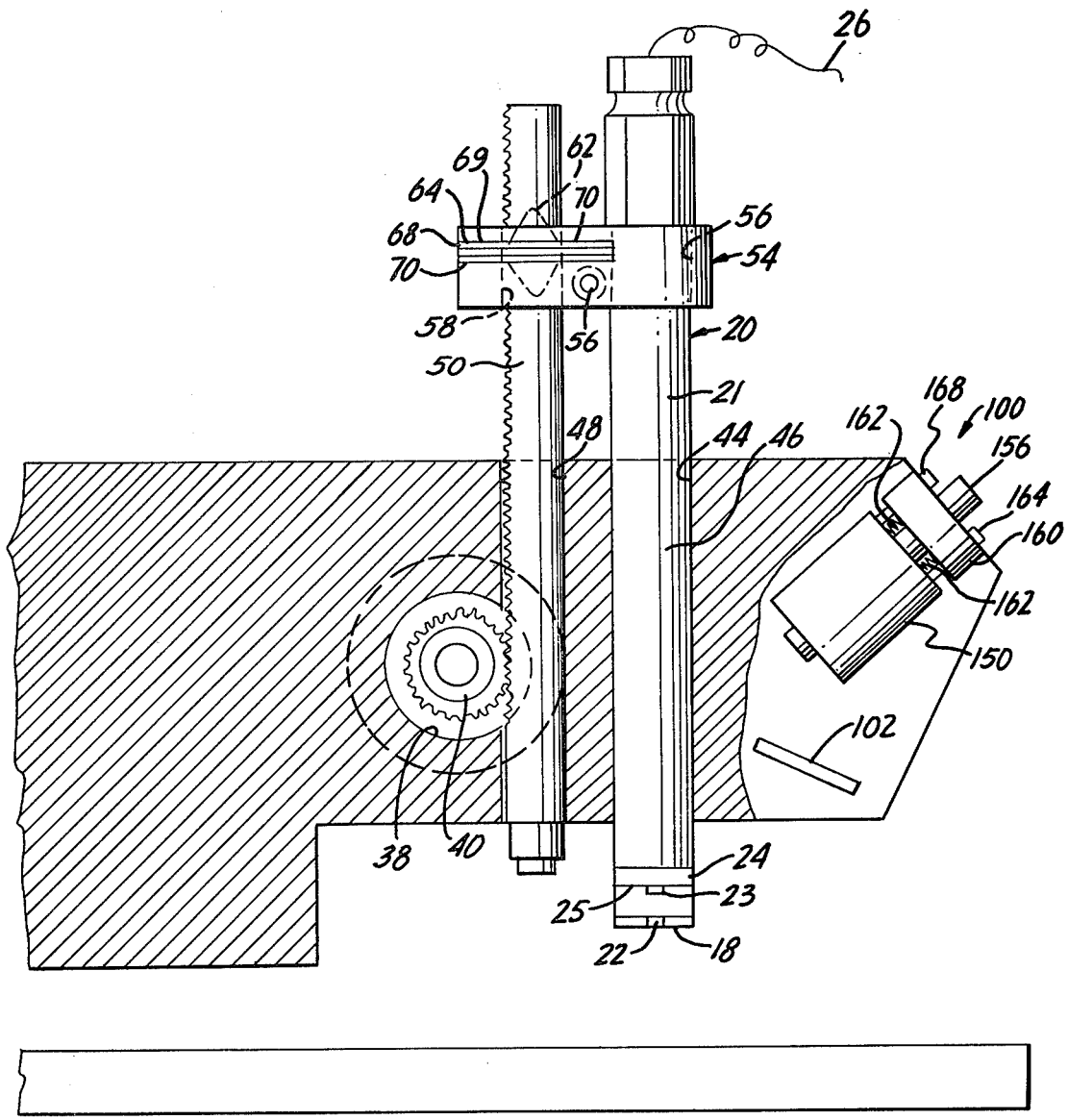
FIG. 3A is a section taken on the line 3A—3A of FIG. 4.
Figure 3B:
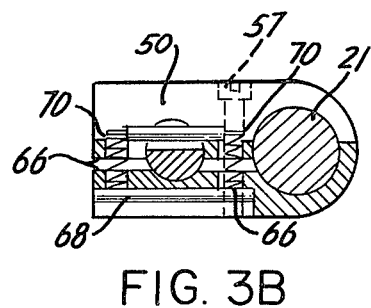
FIG. 3B is a section taken on the line 3B—3B of FIG. 3.
Figure 4:
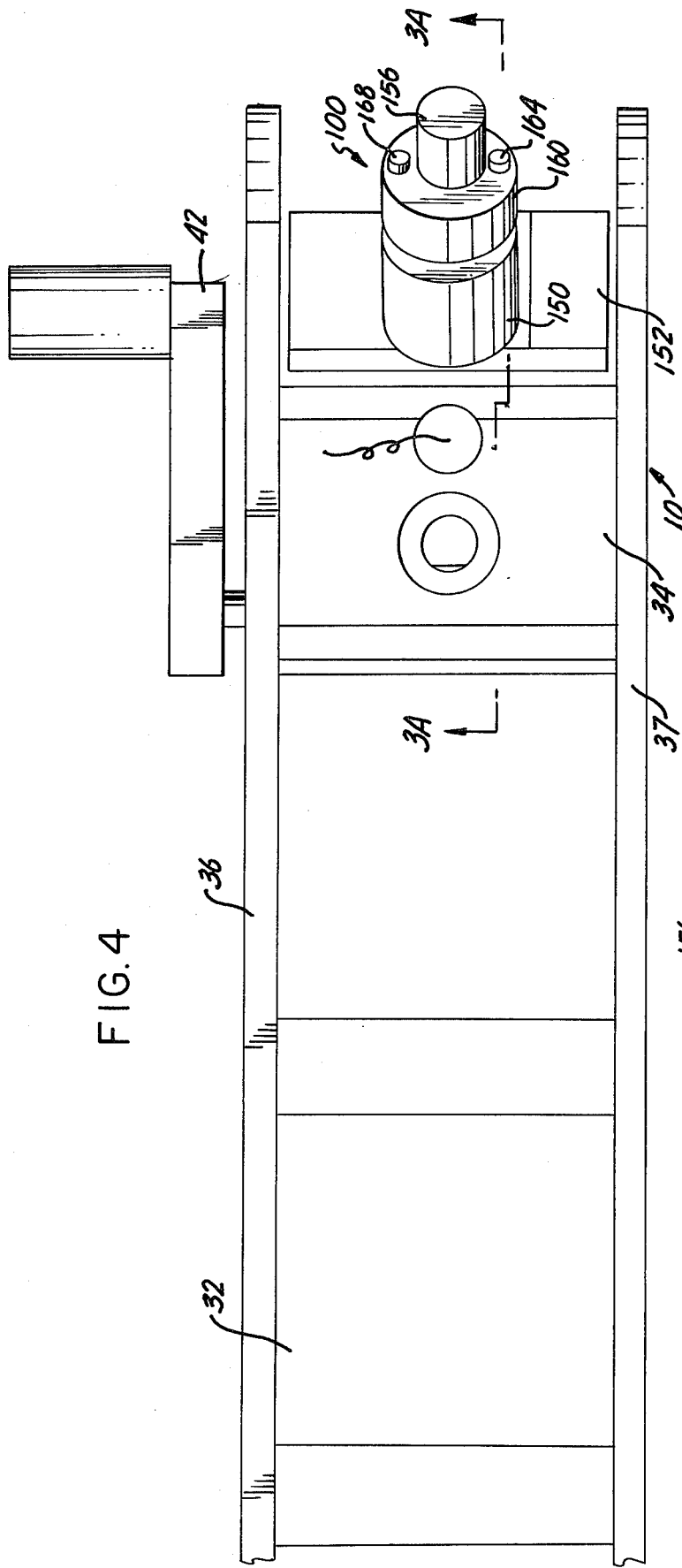
FIG. 4 is a plan view of the apparatus illustrated in FIG. 3.
Figure 5:
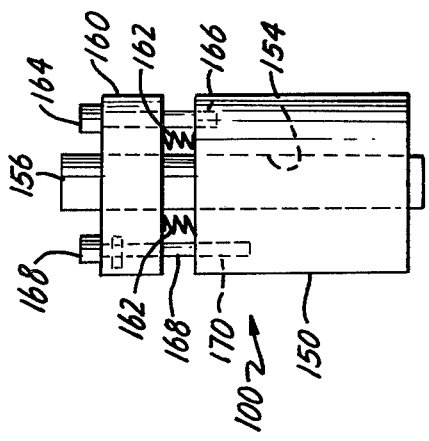
FIG. 5 is a schematic side elevational view of the reticle unit.

Referring now to FIGS. 3 and 4 and as disclosed in greater detail in said U.S. Pat. No. 3,720,833, it will be seen that the measuring apparatus 10 includes an elongate housing 32, the end of which has a central guide body 34 fixedly secured to a pair of opposing side walls 36 and 37. A horizontal bore 38 extends completely across the guide body and a pinion member 40 is rotationally supported by the opposing side walls and positioned therein. A crank handle 42 controls the movement of the pinion member.

Two vertically extending bores are defined in the guide body. A first of these vertical bores 44 extends from the top to the bottom of the guide body and is selectively sized and shaped so as to slidingly receive a probe assembly 46 of the character described above. The second of these vertical bores 48 which also extends the entire vertical dimension of the guide body is selectively sized and shaped so as to slidingly receive a toothed rack member 50 which engages the pinion 40 and is controlled thereby.

The probe assembly 46 is mounted on the toothed rack of the rack and pinion assembly by means of a coupling 54. The coupling 54 has first 56 and second 58 cylindrical bores which extend from the top surface to the bottom surface thereof. A vertically extending slit 60 is established in the coupling and extends vertically from the top to the bottom surface thereof and horizontally from one side thereof, through one of the bores 58 to the other bore 56 thereby defining opposing coupling portions which are integral at the other end thereof. The coupling is made from a resilient material and the two coupling portions may be drawn together, with the solid end of the coupling functioning as a hinge, by a bolt 57 which extends through one portion of the coupling and is threadedly engaged with the other coupling portion. The first bore 56 is selectively sized so that when the two coupling portions are drawn together subsequent to the positioning of the probe assembly therewithin, the probe assembly will be compressively located within this first coupling bore 56 and will become integral therewith. The second coupling bore 58 is selectively sized so as to allow vertical displacement of the toothed rack therethrough when the coupling is integral with the probe assembly. The two coupling portions may be separate pieces which are hingedly joined.

The toothed rack has a horizontally extending V-shaped notch 62 and each coupling portion has a horizontal slot 64 which extends in a direction substantially parallel to the base of the V-shaped notch and a pair of bores 66 which extend perpendicularly thereto establishing a pair of continuous bores extending through the coupling from one slot to the other. A bar 68 is positioned in one slot and is attached by a pair of springs 70 which extend through the aligned bores 66 of the coupling portions to a rolling pin 72 which is positioned in the other slot. The slot in which the rolling pin is positioned has sufficient depth so that the rolling pin which is forcefully urged by the springs against the rack member can roll up the inclined surface of the V-shaped notch and along the outer surface of the rack member when the coupling is displaced vertically relative to the toothed rack. Such relative displacement may occur when the displacement of the portable probe assembly is blocked. When the portable probe assembly is free to move, the compressive force exerted by the springs 70 is sufficient to maintain the rolling pin proximate the base of the V-shaped notch 62 and accordingly the portable probe assembly and the rack will then be displaced as a unit.

Turning of probe casing 21 in bore 44 may be prevented by providing such bore and the casing with noncircular cross-sections or with a noncircular configuration with a complementally shaped sleeve secured to the probe casing 21 or by any other suitable means such as a clamp to prevent undesired probe rotation.

In order to permit any selected area of the workpiece that is to be subjected to beta radiation to be precisely positioned for interfacial engagement with the aperture 22 in the mask 18 on the dependent end of the probe 21, an improved optical locating system, generally designated 100, is provided on the outboard side of the housing. Such optical locating system is adapted to provide a reticular image that is identical, both as to size, shape and location, with the area to be exposed to beta radiation, as the latter is defined by the aperture 22 in mask 18, in superposed relation with a workpiece when said mask is disposed remote therefrom. Such system thus permits visual orientation of a workpiece at the operating location in precise position for subsequent exposure of the selected area thereof to beta radiation.

Included in such locating system is a beam splitting mirror element 102 positioned in predetermined offset angular relation to a measuring location 104 in the path of advance of the probe element 21 which is readily observable by the operator from the exposed end of the instrument. A magnifying lens 106, pivotally mounted as at 108, may be included to provide a magnified view of the workpiece.

Figure 2:
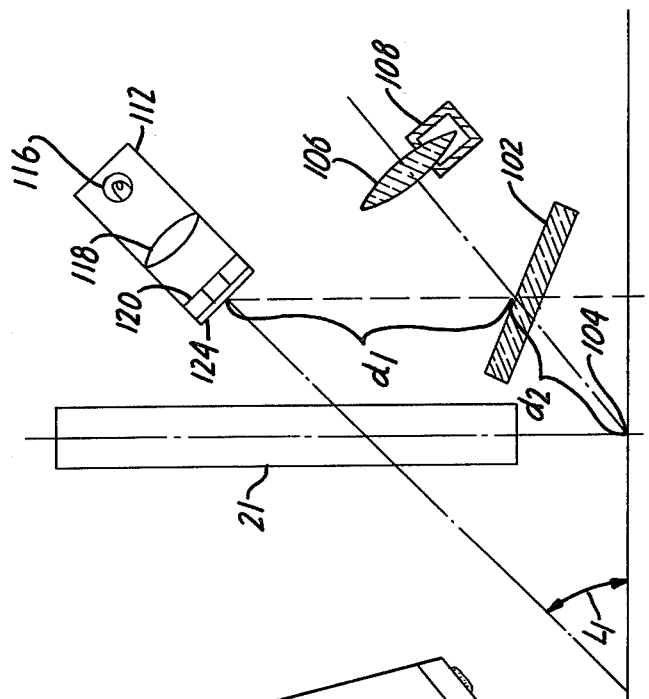
FIG. 2 is a schematic side elevational view of the components of the improved optical system incorporated in the instrument of FIG. 1.

In association with the beam splitting mirror 102 is a reticle assembly, generally designated 112. Such reticle assembly includes a cylindrical mounting block or bushing 150 fixedly mounted in the end plate 152 of housing 32 and having a central bore 154. Disposed within the bore 154 is a tubular housing 156 for a light source 116. As best shown in FIG. 2, such housing 156 has the light source 116 disposed at the upper end thereof, an intermediate light concentrating lens 118 and a mask 120 disposed at the other terminal end thereof. The mask 120 includes an aperture therein that is of the same size and shape as the exposure during aperture 22 in the mask 18 at the end of probe 21. Such mask 120 is mounted in the light housing 156 in such manner as to be readily removable and replaced by another mask element having a different exposure area defining aperture therein in conformity with that associated with the probe element. Preferably a layer of light diffusing media 124 is disposed in overlying interfacial relation with the mask 120.

The housing 156 is selectively positionable along its longitudinal axis so as to accommodate differing workpiece thicknesses and to properly position the image of the aperture 122 in mask 120 in overlying relation with the view of the portion of the workpiece disposed at the measuring location 104 as the latter appears when viewed through the reflective surface of the beam splitting mirror 102. Such limited longitudinal adjustability is conveniently achieved by mounting the upper end of the light housing 156 in an adjusting collar 160 disposed in spaced relation with the bushing 150 and biased in separated relation thereto by springs 162. One limiting position is determined by adjusting screw 164 having its dependent end 166 disposed in threaded engagement with a bore in bushing 150. Longitudinal adjustment is effected by a second screw 168 connected to collar 160 and having its threaded end disposed in threaded engagement with a second bore 170 in bushing 150, the depth of which is determinative of the other limiting position for the light housing 156.

The optics of this system function in accordance with the ordinary laws of reflection and refraction. The reticle assembly is prepositioned in alignment with the center line of the probe 21 and at an angle $L_1$ relative to the horizontal, such that the image of the back-lighted aperture 122 on the upper surface of the beam splitting mirror can be viewed without parallax effects. Additionally, the distance $d_1$ is approximately the same as the distance $d_2$ between the locus of workpiece exposure 104 and the upper surface of the beam splitting mirror 102. Longitudinal adjustment of the position of the light housing 156 of the reticle assembly serves to accommodate different workpiece thicknesses. The angle of the beam splitting mirror 102 is fixed to permit viewing of the reticular image of the aperture in superposed relation with the workpiece surface without parallax effects. When the reticle assembly elements are properly positioned, the operator will see the reticular image of the aperture 122, which is identical with that of the aperture 22 in probe mask 18, in superposed relation with the surface of the workpiece at the measurement location 104 in the direct path of advance of the probe 21.

As will now be apparent in the operation of the device, the operator will adjust the positioning of the workpiece relative to the image of the aperture 122 as reflected from the surface of the beam splitting mirror 102 until the desired area of the workpiece to be exposed to radiation is properly aligned therewith. When the workpiece is so positioned, the crank 42 is manipulated so as to downwardly displace the probe 21 into interfacial contact with the workpiece. Since the aperture 122 in the mask 120 in the reticle assembly has been geometrically prealigned to provide an image that is identical in size, shape and positioning with the aperture 22 in the probe mask 18 when the latter is lowered into interfacial engagement with the workpiece, the latter aperture will be displaced into exact superposed relation with the observed image and the coincident area on the prepositioned workpiece will be thus exposed to radiation for measurement of coating thickness therein.

As will now also be apparent to those skilled in this art, the above described system permits the operator of the instrument to see the area of exposure directly upon the workpiece surface and with a reticular image of any predetermined desired size or configuration. Apart from the general accuracy of workpiece positioning that derives therefrom, the system significantly expands the effectiveness of beta backscatter measuring equipment in that, inter alia, it permits accurate measurements closely adjacent the marginal edges of coatings, permits measurement of varying coating configurations through visual correspondence between areas of exposure and workpiece surface.

Having thus described our invention, we claim:

1. A beta backscatter type of thickness measuring instrument comprising
   a workpiece supporting platform,
   a probe assembly including a beta ray isotope source and a first mask defining a selectively contoured exposure area disposed adjacent thereto,
   means for advancing said probe assembly along a predetermined path to place said mask in interfacially engaged relation with the surface of a workpiece disposed on said workpiece supporting surface,
   a beam splitting mirror for providing a transmitted image of the portion of the workpiece surface disposed in the path of advance of said probe assembly at a remote location,
   a reticle assembly including a second mask identically defining said selectively contoured exposure area and a light source for back illuminating said mask,
   means for selectively prepositioning said back illuminated sound mask relative to said beam splitting mirror to provide a reflected image of said exposure area at the surface of said beam splitting mirror in superposed relation to said transmitted image of said workpiece surface that is indicative of the location of the exposure area to be defined by said first mask when the latter is disposed in interfacial engagement with said workpiece surface,
   whereby said workpiece may be moved relative to said reflected image to precisely locate the surface area thereof that is to be exposed to radiation through said first mask when the latter is disposed remote therefrom.

2. An instrument as set forth in claim 1 further including means for displacing said reticle assembly in a direction parallel to its longitudinal axis to accommodate workpieces of varying thickness.

3. A workpiece positioning system for beta backscatter type of thickness measuring instruments wherein a first mask defining a selectively contoured exposure area is advanced along a predetermined path into interfacial engagement with a workpiece to define the surface area thereof to be exposed to beta radiation, comprising a beam splitting mirror for providing a transmitted image of the workpiece surface at a remote location therefrom, a reticle assembly including a second mask identically defining said selectively contoured exposure area and means for back illuminating said mask, means for positioning said back illuminated mask relative to said beam splitting mirror and to the path of advance of said first mask to provide a reflected image of said exposure area at the surface of said beam splitting mirror in superposed relation to the transmitted image of said workpiece surface, whereby said workpiece may be moved to precisely locate the surface area thereof that is to be exposed to radiation through said first mask through visual superposition of said reflected image thereon.

4. A workpiece positioning system as set forth in claim 3 wherein said reticle assembly is adjustably positionable to accommodate workpieces of varying thickness.

5. A workpiece positioning system as set forth in claim 3 including means disposed adjacent said mask for diffusing the back illumination thereon.

* * * * *